United States Patent
Yamamoto et al.

(10) Patent No.: US 8,779,193 B2
(45) Date of Patent: Jul. 15, 2014

(54) METHOD FOR PRODUCING A PURIFIED BORAZINE COMPOUND, METHOD FOR FILLING A BORAZINE COMPOUND, AND CONTAINER FOR PRESERVING A BORAZINE COMPOUND

(75) Inventors: Tetsuya Yamamoto, Nishinomiya (JP); Yasutaka Nakatani, Higashiosaka (JP); Hiroko Harada, Osaka (JP)

(73) Assignee: Nippon Shokubai Co., Ltd., Osaka (JP)

( * ) Notice: Subject to any disclaimer, the term of this patent is extended or adjusted under 35 U.S.C. 154(b) by 299 days.

(21) Appl. No.: 12/952,610

(22) Filed: Nov. 23, 2010

(65) Prior Publication Data

US 2011/0065956 A1  Mar. 17, 2011

Related U.S. Application Data

(62) Division of application No. 11/346,551, filed on Feb. 2, 2006, now Pat. No. 7,855,307.

(30) Foreign Application Priority Data

Aug. 23, 2005 (JP) ................. 2005-241389
Aug. 30, 2005 (JP) ................. 2005-250074

(51) Int. Cl.
  *C07F 5/05* (2006.01)
(52) U.S. Cl.
  USPC .......................................................... 564/10
(58) Field of Classification Search
  None
  See application file for complete search history.

(56) References Cited

U.S. PATENT DOCUMENTS

| 3,242,139 | A | 3/1966 | Long et al. |
| 4,094,669 | A | 6/1978 | Balko et al. |
| 5,409,526 | A * | 4/1995 | Zheng et al. ............. 96/132 |
| 5,707,536 | A | 1/1998 | Meissner |
| 7,617,934 | B2 | 11/2009 | Taguchi et al. |
| 2005/0177002 | A1 | 8/2005 | Yamamoto et al. |

FOREIGN PATENT DOCUMENTS

| GB | 913862 | 12/1962 |
| JP | 20007622 A | 1/2000 |
| JP | 2001-341794 A | 12/2001 |
| KR | 20050004074 A | 1/2005 |

OTHER PUBLICATIONS

Hohnstedt, L. et al. "Preparation of N-trisubstituted borazines by reduction of B-trichloroborazines," JACS (1960) 82: 89-92.*
G.E. Ryschkewitsch et al., "The Chemistry of Borazene .I. The Reaction of B-Trichloro-N-trimethylborazene with Grignard Reagents." J. Am. Chem. Soc., 1958, vol. 80, pp. 4515-4517.
Hough et al. The preparation, Identification and Characterization of N-Trialkylborazoles, J. Am. Chem. Soc., 1955, vol. 77, pp. 864-865.
Chemical Handbook, Applied Chemistry, edited by The Chemical Society of Japa, published on Jan. 30, 2003, by Maruzen C., Ltd. the 6$^{th}$ Edition, p. 576-578 (Partial English Translation Enclosed).
Official Notice of Reason for Refusal for Japanese Application 2005-250074 dated Jan. 18, 2011, 4 pages. (English translation enclosed; 3 pages.).
Official Action for Taiwanese Application No. 095103269 dated Aug. 16, 2011, 9 pages.
Ryschkewitsch et al., "The Chemistry of Borazene I. The Reaction of B-Trichloro-N-trimethylborazene with Grignard reagents." Sep. 5, 1958.
Bradley et al., "The chemistry of Borazene. I. The reaction of B-Trichloro-N-Trialkozyborazenes and N-Trimethyld-B-Triphenoxyborazene", J.Am. Chem. Soc.81:2635-2638, 1959, XP002373704.
Meller et al., "1,3,5-Trimethyl-und 1,3,5-Tri[methyl($d_3$)]borazinderivate", Monatshefte Fur Chemie, Springer Verlag/ Wien. 98:513-523, 1967, XP008061560.
Meller, "Die Reaktion von Aminoborazinen mit Diboran", Monatshefte Fuer Chemis, 99:1670-1679, 1968, XP008061946.
Wideman et al., "39. Borazine, Polyborazylene, B-Vinylborazine, and Poly(B-Vinylborazine)", Inorganic Syntheses, 32:232-242, 1998, XP 008061852.
Meller, Gmelin Handbuch der Anorganischen Chemie Band 51, pp. 36-55, 72-83, 130-159, 1978.
Muetterties, Boron Hydride Chemistry, pp. 241-272, 1975.
Steinberg, Organic Chemistry vol. 2, pp. 221-231, 244-266, 1996.
Turbini, A. et al. "Photochemical Study of the N-Methylborazine." Inorganic Chemistry, vol. 14, No. 6, 1975, pp. 1252-1257.

* cited by examiner

*Primary Examiner* — Sudhakar Katakam
(74) *Attorney, Agent, or Firm* — Cesari and McKenna, LLP

(57) ABSTRACT

On producing a purified borazine compound, a borazine compound is filtrated under an atmospheric condition of a water content of not higher than 2000 volume ppm. Or, on filling a borazine compound into a container, the above described borazine compound is filled into the above described container under an atmospheric condition of a water content of not higher than 2000 volume ppm. Or, as a container for preservation for preserving a borazine compound, a container for preserving a borazine compound, which has withstanding pressure of not lower than 0.1 MPa, is used.

13 Claims, No Drawings

METHOD FOR PRODUCING A PURIFIED BORAZINE COMPOUND, METHOD FOR FILLING A BORAZINE COMPOUND, AND CONTAINER FOR PRESERVING A BORAZINE COMPOUND

CROSS-REFERENCE TO RELATED APPLICATIONS

This application is a division of U.S. application Ser. No. 11/346,551, filed on Feb. 2, 2006, claiming priority to Japanese Patent Application No. 2005-241389, filed Aug. 23, 2005; and Japanese Patent Application No. 2005-250074, filed Aug. 30, 2005, the content of which is hereby incorporated by reference in its entirety.

BACKGROUND OF THE INVENTION

1. Field of the Invention

The present invention relates to borazine compounds. Borazine compounds are used to form, for example, an interlayer dielectric film for semiconductor, a barrier metal layer and an etching stopper layer.

2. Description of Related Art

With higher functionalization of information devices, design rule of LSI has been required to be finer year by year. In production of LSI with finer design rule, materials composing LSI should also have higher performance and fulfill function even on fine LSI.

For example, as for materials used for an interlayer dielectric film in LSI, high dielectric constant causes signal delay. In fine LSI, effects of the signal delay is particularly significant. Therefore, development of a new low dielectric material which can be used for an interlayer dielectric film has been needed. Also, it is necessary not only to have low dielectric constant but also superior characteristics such as humidity resistance, heat resistance, mechanical strength, etc. to be used as an interlayer dielectric film.

As a material to respond to these requirements, a compound having borazine ring backbone has been proposed (for example, see US Laid Open Patent No. 2002-58142). A compound having borazine ring backbone (borazine compound) has small molecular polarizability and thus a coated film formed provides low dielectric constant. Moreover, the coated film formed is superior in heat resistance.

As a borazine compound, various compounds have been proposed up to now. For example, an alkylborazine compound, whose boron moiety is substituted with an alkyl group, has very superior characteristics as low dielectric constant material (for example, see US Laid Open Patent No. 2003-100175).

BRIEF SUMMARY OF THE INVENTION

Here, when a borazine compound is used, for instance, as an interlayer dielectric film for semiconductor as stated above, it is preferable that impurities in a borazine compound used are fewer. For example, in case of using it as an interlayer dielectric film of a semiconductor, when impurities in a borazine compound used are too much, there is fear that the function of an interlayer dielectric film, or the like obtained is lowered. On the contrary, when impurities in a borazine compound used are few, occurrence of such problems as stated above can be suppressed.

The present inventors have found that a contaminating source of impurities which may cause lowering of the function of an interlayer dielectric film or the like as stated above is, for example, impurities in air on production of a borazine compound, filling thereof into a container, or conveyance thereof or the like, as a cause thereof. Also, the present inventors have found that contact with moisture of a borazine compound may become a cause of contamination of impurities. Namely, the present inventors have found that when a borazine compound (for example, N,N',N"-trimethylborazine) contacts with moisture, N—B bond is hydrolyzed, and a decomposed product (for example, methylamine and a boric acid) generates as impurities.

Conventionally, as for a borazine compound, only a small amount thereof in a laboratory scale was synthesized, and it is usually preserved in a reagent bottle, or the like. On the other hand, when mass production thereof from now is taken into consideration, it is thought that necessity of preserving it in a larger container for a long period will be caused.

Here, on preserving a borazine compound which was mass-produced, a case of adopting as a container for preservation a drum or the like which is used for preserving a general compound, is considered. Such a container usually breathes under an atmosphere to the extent of an atmospheric pressure, and a gas in a container and an outer gas comes and goes to some extent at an inside and an outside of the container. Therefore, when a container used conventionally generally for preserving a compound is attempted to use for preserving a borazine compound as it is, there is possibility that moisture contained in an outer gas flows into the container accompanied with flowing into the container of an outer gas, and decomposition of a borazine compound is caused.

As stated above, there is fear that impurities are contaminated into said compound in many processes of production of a borazine compound, filling thereof into a container, conveyance or preservation thereof. However, as means for removing effectively such impurities contaminated, satisfactory means have not yet been proposed, and development of such means is waited for, which is the present status.

An object of the present invention is to provide a mean for suppressing effectively the contamination of impurities into said compound on production of a borazine compound and on filling a borazine compound produced into a container.

Another object of the present invention is, on preserving a borazine compound, to provide a mean for suppressing the flowing of an outer gas containing moisture into a container for preservation and to prevent decomposition of a borazine compound on preservation.

Still another object of the present invention is to provide a borazine compound having a small content of impurities.

The present inventors have intensively studied to accomplish the objects described above. As the result, the present inventors have found that on production or filling of a borazine compound, contamination of impurities in a borazine compound can be suppressed by controlling a content of moisture in an atmosphere on production or filling of a borazine compound. Further, the present inventors have found that contamination of impurities in a borazine compound can be suppressed by controlling a withstanding pressure of a container for preservation used for preserving a borazine compound to not lower than a predetermined value.

Namely, according to an aspect of the present invention, a method for producing a purified borazine compound, which has a borazine compound preparatory step wherein a borazine compound is prepared, and a filtration step wherein the above described borazine compound prepared is filtrated under an atmospheric condition of a water content of not higher than 2000 volume ppm, is provided.

According to another aspect of the present invention, a borazine compound in which a content of impurities having a particle diameter of not smaller than 0.5 μm is not higher than 100 particles/mL, is provided.

According to further another aspect of the present invention, a method for filling a borazine compound, which has a filling step wherein a borazine compound is filled into a container under an atmospheric condition of water content of not higher than 2000 volume ppm, is provided.

According to further another aspect of the present invention, a container for preserving a borazine compound, which has withstanding pressure of not lower than 0.1 MPa, is provided.

According to further another aspect of the present invention, a borazine compound in which decrease of purity in case of preserving at 25° C. for 60 days is not higher than 1% by mass, is provided.

DETAILED DESCRIPTION OF THE INVENTION

One aspect of the present invention relates to a technique for suppressing contamination of impurities into a borazine compound on production of said compound. Specifically, said aspect of the present invention is a method for producing a purified borazine compound, which has a borazine compound preparatory step wherein a borazine compound is prepared, and a filtration step wherein the above described borazine compound prepared is filtrated under an atmospheric condition of a water content of not higher than 2000 volume ppm.

In a method of production of the present aspect, a borazine compound is filtrated under an atmospheric condition having specified water content. Thereby, contamination of impurities into a purified borazine compound can be suppressed effectively.

Subsequently, a method for production of the present aspect is explained in detail in the order of processes.

[A Borazine Compound Preparatory Step]

In a method for production of the present aspect, first of all, a borazine compound is prepared.

Specific embodiments of a borazine compound prepared are not particularly limited, and conventionally known knowledge may be referred appropriately. The borazine compound is represented, for example, by the chemical formula 1 described below.

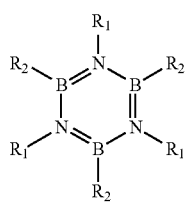

Chemical formula 1 wherein $R^1$ and $R^2$ may be respectively the same or different, and are a hydrogen atom or an alkyl group. The alkyl group may be any of straight chain, branched or cyclic type. Carbon atoms of the alkyl group are not especially limited, however, preferably 1 to 8, more preferably 1 to 4 and further preferably 1. Specific examples of the alkyl group include a methyl group, an ethyl group, a propyl group, an isopropyl group, a butyl group, an isobutyl group, a sec-butyl group, a tert-butyl group, a pentyl group, an isopentyl group, a neopentyl group, a hexyl group, a heptyl group, an octyl group, a nonyl group, a decyl group, a cyclopropyl group, a cyclopentyl group and a cyclohexyl group. Alkyl groups other than these may also be used. And examples of a borazine compound include borazine, N,N',N''-trimethylborazine, N,N',N''-triethylborazine, N,N',N''-tri(n-propyl)borazine, N,N',N''-tri(iso-propyl)borazine, N,N',N''-tri(n-butyl)borazine, N,N',N''-tri(sec-butyl)borazine, N,N',N''-tri(iso-butyl)borazine, N,N',N''-tri(tert-butyl)borazine, N,N',N''-tri(1-methylbutyl)borazine, N,N',N''-tri(2-methylbutyl)borazine, N,N',N''-tri(neo-pentyl)borazine, N,N',N''-tri(1,2-dimethylpropyl)borazine, N,N',N''-tri(1-ethylpropyl)borazine, N,N',N''-tri(n-hexyl)borazine, N,N',N''-tricyclohexylborazine, N,N'-dimethyl-N''-ethylborazine, N,N'-diethyl-N''-methylborazine, N,N'-dimethyl-N''-propylborazine, B,B',B''-trimethylborazine, B,B',B''-triethylborazine, B,B',B''-tri(n-propyl)borazine, B,B',B''-tri(isopropyl)borazine, B,B',B''-tri(n-butyl)borazine, B,B',B''-tri(isobutyl)borazine, B,B',B''-tri(tert-butyl)borazine, B,B',B''-tri(1-methylbutyl)borazine, B,B',B''-tri(2-methylbutyl)borazine, B,B',B''-tri(neopentyl)borazine, B,B',B''-tri(1,2-dimethylpropyl)borazine, B,B',B''-tri(1-ethylpropyl)borazine, B,B',B''-tri(n-hexyl)borazine, B,B',B''-tricyclohexylborazine, B,B'-dimethyl-B''-ethylborazine, B,B'-diethyl-B''-methylborazine, and B,B'-dimethyl-B''-propylborazine.

In this connection, when stability such as water resistance and a handling property of a borazine compound produced are considered, a borazine compound preferably is an N-alkylborazine.

Further, a borazine compound prepared may be an alkylborazine wherein a nitrogen moiety and a boron moiety are substituted with an alkyl group (namely, both of $R^1$ and $R^2$ are an alkyl group) which includes B,B',B''-trimethyl-N,N',N''-trimethylborazine, B,B',B''-trimethyl-N,N',N''-triethylborazine, and B,B',B''-triethyl-N,N',N''-trimethylborazine.

A route for obtaining a borazine compound to be prepared is not especially limited. When a commodity of a borazine compound is commercially available, said commodity which is purchased may be used, or a borazine compound prepared personally may be used.

A method for preparing personally a borazine compound also is not especially limited. One example of a method for preparing a borazine compound represented by Chemical formula 1 described above includes a method for reacting in a solvent an alkali boron hydride represented by $ABH_4$ (wherein A is a lithium atom, a sodium atom, or a potassium atom) with an amine salt represented by $(RNH_3)_nX$ (wherein R is a hydrogen atom or an alkyl group, X is a sulfuric acid group or a halogen atom, and n is 1 or 2).

In an alkali boron hydride ($ABH_4$), A is a lithium atom, a sodium atom, or a potassium atom. Examples of an alkali boron hydride include sodium boron hydride and lithium boron hydride.

In an amine salt represented by $(RNH_3)_nX$, R is a hydrogen atom or an alkyl group, and X is a sulfuric acid group or a halogen atom. And when X is a sulfuric acid group, n is 2, and when X is a halogen atom, n is 1. When n is 2, R may be the same or different as stated above. Considering yield of a synthesis reaction or easiness of handling, R preferably is the same alkyl group. The alkyl group may be any of straight chain, branched or cyclic type. Carbon atoms of the alkyl group are not especially limited, however, preferably 1 to 8, more preferably 1 to 4 and further preferably 1. Specific examples of the alkyl group include a methyl group, an ethyl group, a propyl group, an isopropyl group, a butyl group, an isobutyl group, a sec-butyl group, a tert-butyl group, a pentyl group, an isopentyl group, a neopentyl group, a hexyl group, a heptyl group, an octyl group, a nonyl group, a decyl group, a cyclopropyl group, a cyclopentyl group, and a cyclohexyl group. Alkyl groups other than these may also be used. Examples of the amine salt include ammonium chloride ($NH_4Cl$), monomethylamine hydrochloride ($CH_3NH_3Cl$), monoethylamine hydrochloride ($CH_3CH_2NH_3Cl$), monomethylamine hydrobromide ($CH_3NH_3Br$), monoethylamine hydrofluoride ($CH_3CH_2NH_3F$), ammonium sulfate (($NH_4)_2SO_4$), and monomethylamine sulfate (($CH_3NH_3)_2SO_4$).

An alkali boron hydride and an amine salt used may be selected in accordance with a structure of a borazine compound synthesized. For example, when N-methylborazine wherein a methyl group is bonded to a nitrogen atom composing a borazine ring, is produced, as an amine salt, an amine salt wherein R is a methyl group such as monomethylamine hydrochloride, may be used.

A mixing ratio of an alkali boron hydride and an amine salt is not particularly limited, but when an amount used of an amine salt is supposed to be 1 mol, an amount used of an alkali boron hydride is preferably 1 to 1.5 mol.

A solvent for synthesis is not particularly limited, and for example, tetrahydrofuran, monoethylene glycol dimethyl ether (monoglyme), diethylene glycol dimethyl ether (diglyme), triethylene glycol dimethyl ether (triglyme) and tetraethylene glycol dimethyl ether (tetraglyme) are included.

A reaction condition of an alkali boron hydride and an amine salt is not particularly limited. A reaction temperature is preferably 20 to 250° C., more preferably 50 to 240° C., further preferably 100 to 220° C. When a reaction is conducted in the range as described above, a content of hydrogen generated is easily controlled. A reaction temperature can be measured by using a sensor of temperature such as a K-thermocouple.

On the other hand, an alkylborazine compound can be synthesized by taking a halogenated borazine compound such as B,B',B"-trichloro-N,N',N"-trialkylborazine as a starting material, and by substituting a chlorine atom of said compound with an alkyl group using a Grignard reagent (see D. T. HAWORTH and L. F. HOHNSTEDT, J. Am. Chem. Soc., 82, 3860 (1960)).

A borazine compound synthesized can be purified in accordance when needed. As a method for purification, for example, distillation purification is used.

A scale and a type of distillation purification equipment may be determined in response to environment or a scale. For example, to treat a large quantity of a borazine compound, an industrial scale distillation column may be used. On the other hand, to treat a small quantity of a borazine compound, distillation purification using a distillation tube can be used. For example, as a specific example of equipment for distillation to treat a small quantity of a borazine compound, distillation equipment attached with a Liebig cooling tube by a Claisen type connecting tube to a 3-neck flask may be used. However, a technical scope of the present invention is by no means limited to practical embodiments using these equipments for distillation.

Temperature on distillation purification is not particularly limited, and may be appropriately set in accordance with kinds of a borazine compound synthesized. As one example, it is usually set at around 100 to 150° C.

[A Filtration Step]

Successively, a borazine compound prepared in the above-described is filtrated. Thereby, impurities can be separated and a borazine compound is further purified, and production of a purified borazine compound is completed.

In a method of the present aspect, this filtration step is conducted in an atmospheric condition wherein a water content thereof is not higher than a specified value.

Specifically, a water content in the above-described atmosphere is not higher than 2000 volume ppm, preferably not higher than 1000 volume ppm, more preferably not higher than 500 volume ppm, further preferably not higher than 100 volume ppm, particularly preferably not higher than 10 volume ppm, most preferably not higher than 1 volume ppm. As stated above, a borazine compound is weak to water, and when a water content in an atmosphere is much, there is fear that a borazine compound decomposes by contacting with water, and impurities are contaminated into a borazine compound. Therefore, according to the present invention, decomposition of a borazine compound by contacting with water is suppressed, and efficiency of purification of a borazine compound can be improved. In this connection, as a method of making a water content in an atmosphere to not higher than 2000 volume ppm, for example, a method of displacing with a gas of which a dew point is controlled, can be used. Incidentally, as a value of water content in an atmosphere conducted at a filtration step, a value measured by a method adopted in Examples as stated later is adopted.

Further, in the present invention, cleanliness in an atmosphere also preferably is controlled to not higher than a specified value.

Here, "cleanliness" means a number of a foreign material having a size of not smaller than 0.1 μm residing in 1 cubic feet (1 $ft^3$). In the method described above according to the present invention, the filtration step is conducted in an atmosphere wherein a number of a foreign material having a size of not smaller than 0.1 μm residing in 1 $ft^3$ is preferably not higher than 1000, more preferably not higher than 100, and further preferably not higher than 10, and particularly preferably not higher than 1. Herein, as a method of making cleanliness in an atmosphere to not higher than 1000, for example, a method of air filtration with a filter can be used. Incidentally, as a value of cleanliness in an atmosphere conducted at a filtration step, a value measured by a method adopted in Examples as stated later is adopted.

Other specific embodiments of an atmosphere conducted at a filtration step are not especially limited, but the filtration step preferably is conducted under an atmosphere of a rare gas such as argon or an inactive gas such as nitrogen.

Specific embodiments of filtration means used to obtain a purified borazine compound conducted at a filtration step are not especially limited. One example thereof includes an embodiment wherein a borazine compound is purified with a filtration filter. In this case, a mesh opening size of a filtration filter is not especially limited, and preferably is 0.01 to 1 μm, and more preferably 0.1 to 0.5 μm. When a mesh opening size of a filtration filter is too small, there is fear that clogging is soon caused, and the filtration step does not smoothly proceed. On the other hand, when a mesh opening size of a filtration filter is too large, there is fear that impurities in a compound are not sufficiently removed. Furthermore, a constituent material of a filtration filter also is not especially limited, but from the viewpoint of enabling to sufficiently suppress contamination of impurities, the filtration filter preferably is composed of a resin. A resin material composing the filtration filter includes, for example, a polytetrafluoroethylene (PTFE), a polypropylene, and the like. Among them, from the viewpoint of effectively suppressing contamination of organic impurities, PTFE is preferably used as a constituent material of the filtration filter.

A flow velocity of a borazine compound on filtrating by passing through a filtration filter also is not especially limited. However, it is preferably 0.01 to 1000 $cm^3$/sec, more preferably 1 to 100 $cm^3$/sec. When the flow velocity is too small, a period of filtration becomes longer, and therefore there is fear that production cost is increased. On the contrary, when the flow velocity is too large, there is fear that contamination of impurities cannot be sufficiently suppressed.

Another aspect according to the present invention relates to a technique for suppressing contamination of impurities on filling a borazine compound into a container. Specifically, said aspect is a method for filling a borazine compound, which has a filling step wherein a borazine compound is filled into a container under an atmospheric condition of a water content of not higher than 2000 volume ppm.

In a filling method according to the present aspect, a borazine compound is filled into a container under an atmosphere having specified water content. Thereby, contamination of impurities on filling of a borazine compound can effectively be suppressed.

Subsequently, the filling method according to the present aspect is explained in the order of processes.

[A Borazine Compound Preparatory Step]

First of all, a borazine compound desired to fill is prepared. A specific embodiment for preparing a borazine compound, and a specific embodiment of a borazine compound thereby prepared can be adopted in the same way as the embodiments explained in the column of [A borazine compound preparatory step] of a production method in the above stated embodiments, and therefore herein details thereof is omitted.

In the present step, preferably, a purified borazine compound produced by a production method, which has the above stated embodiment, is prepared. By using this purified borazine compound, an amount of impurities in a borazine compound filled can be further decreased.

[Filling Step]

Subsequently, a borazine compound prepared in the above described is filled into a container. In a filling method according to the present aspect, this filling step is conducted under an atmospheric condition of a water content of not higher than 2000 volume ppm. Another specific preferable embodiment of an atmosphere conducted in filling step can be adopted in the same way as the embodiment explained in the column of [Filtration step] of a production method in the above stated embodiments, and therefore details thereof are omitted.

In a filling step, a specific embodiment of a container wherein a borazine compound is filled, also is not especially limited. As for a material composing a container, for example, a metallic material such as stainless steel and hastelloy, a plastic material such as PTFE, and the like can be adopted. Among them, a container is preferably composed of stainless steel from the viewpoint that a sealing property thereof is excellent. From the viewpoint of more effectively suppressing contamination of impurities, a container is preferably possible to be sealed, and a means to make a container possible to be sealed is exemplified by an embodiment wherein a portion of a container is provided with a valve, for instance.

In a filling step, a specific embodiment of a filling means which is used to fill a borazine compound is not especially limited. As one example thereof, an embodiment wherein a borazine compound is filled by pressure transferring a borazine compound from a tank wherein a borazine compound is conserved, can be exemplified. In this case, a filling rate on filling a borazine compound to a container is not especially limited. However, it is preferably 0.1 to 100 cm$^3$/sec, more preferably 1 to 10 cm$^3$/sec. When the filling rate is too small, a period of filling becomes longer, and therefore there is fear that production cost is increased. On the other hand, when the filling rate is too large, there is fear that exchange of a container for filling becomes difficult.

According to a production method or a filling method of the present invention, a purified borazine compound wherein a contaminated amount of impurities is reduced than conventional can be provided. Namely, the present invention provides also a purified borazine compound wherein a content of impurities is reduced. In this case, a content of impurities in a purified borazine compound provided by the present invention is not higher than 100 particles/mL, preferably not higher than 50 particles/mL, and further preferably not higher than 10 particles/mL. Herein, "impurities" mean a foreign matter (a substance foreign to a borazine compound) having a particle diameter of not smaller than 0.5 μm. In this connection, it is not saying that the less a content of impurities in a purified borazine compound obtained is, the more preferable. However, a technical scope of a production method of the above stated embodiment according to the present invention is by no means limited to an embodiment wherein a purified borazine compound containing such an amount of impurities is produced. Depending on cases, a purified borazine compound containing impurities outside of this range may be produced. Furthermore, a technical scope of a purified borazine compound containing such a small amount of impurities is by no means limited to a purified borazine compound produced by a production method of the above stated embodiment according to the present invention, and depending on cases, it may be what has been produced by another method. Incidentally, as a content of impurities in a purified borazine compound produced, a value measured by a method described in Examples as stated later is adopted.

According to a further another embodiment of the present invention, a container for preserving a borazine compound, which has withstanding pressure of not lower than 0.1 MPa, is provided. By preserving a borazine compound in such a container, flowing of outer air containing moisture into a container for preservation can be suppressed on preserving a borazine compound, and therefore decomposition of a borazine compound in preservation can be effectively suppressed.

In this connection, "preservation" of a borazine compound is a concept which includes anytime of, from the time when a borazine compound was filled into a container for preservation after synthesis of said compound, to the time when it is used for a specified usage. Therefore, for instance, not only the case where a borazine compound is preserved in a store house in a state of being filled in a container, but also the case where it is transported by a truck or the like in accordance with shipping, are included in the concept of "preservation" according to the present invention. Moreover, a borazine compound may be preserved alone in a container for preservation, but depending on cases, it may be preserved in a container for preservation in a state of being dissolved in a proper solvent, or the like.

Withstanding pressure of a container for preservation according to the present embodiment is not lower than 0.1 MPa as stated above, preferably not lower than 0.2 MPa, and further preferably not lower than 0.3 MPa. In this connection, when the withstanding pressure of a container for preservation is lower than 0.1 MPa, there is fear that on preserving a borazine compound, an atmosphere flows into an inner side of a container, and a borazine compound decomposes owing to contact with moisture contained in the atmosphere. In addition, as a value of withstanding pressure of a container for preserving a borazine compound, a value measured by a method adopted in Examples as stated later is adopted.

"Withstanding pressure" means, when a closed container is put in an atmosphere having a predetermined initial pressure (supposed 0.1 MPa in the present invention) and then pressure of said atmosphere is elevated, pressure which is reduced an initial pressure (0.1 MPa) from pressure of an atmosphere at the point when said atmosphere can flow into an inner side of said container. That means, when pressure of an atmosphere exceeds "withstanding pressure +an initial pressure (0.1 MPa)", said atmosphere may flow into an inner side of a container. Therefore, in the present invention, when a borazine compound is preserved in an atmosphere wherein an initial pressure is 0.1 MPa (approximately equals to an atmospheric pressure), a borazine compound results to be preserved in a container into which said atmosphere does not flow even when pressure of an atmosphere becomes not lower than 0.2 MPa.

Here, from the viewpoint of prevention of flowing of an atmosphere for preservation into an inner side of a container for preservation, an upper limit value of withstanding pressure of a container for preservation is not limited. However, from the viewpoint of easiness of handling such as weight of a container, the withstanding pressure of a container for preservation is preferably not higher than 2.0 MPa, and more preferably not higher than 0.5 MPa. However, embodiments outside of these ranges can be adopted.

Specific embodiments of a size, a material, or the like of a container for preservation are not especially limited. A small container for preservation may be used for preserving a small amount of a borazine compound, which was synthesized for a laboratory level. And a large container for preservation may be used for preserving a large amount of a borazine compound, which was synthesized for an industrial level.

As for a material of a container for preservation, for example, a metallic material such as stainless steel and hastelloy, a plastic material such as a polytetrafluoroethylene (PTFE), and the like can be adopted. Among them, a container is preferably composed of stainless steel, from the viewpoint that withstanding pressure thereof is high. And, for the object of further improving corrosion resistance of a container for preservation, an inner side of the container composed of the above described materials such as a metal should be coated with a resin. In this case, a resin used for coating is not especially limited, and for example, it includes a polytetrafluoroethylene (PTFE), a polypropylene, and the like. Among them, it is preferable to conduct coating with PTFE from the viewpoint that improving effect of corrosion resistance thereof is excellent. Herein, a thickness of coating in resin coating is not especially limited, and is preferably 10 to 3000 μm, more preferably 500 to 1000 μm.

Further, a container for preservation is preferably possible to be sealed, and a means to make a container possible to be sealed is exemplified by an embodiment wherein a portion of a container is provided with a valve, for instance.

In this connection, a temperature condition for preservation on preserving a borazine compound with a container for preservation according to the present aspect cannot be unambiguously defined, since the stability to temperature varies depending on kinds of a borazine compound stability thereof, and therefore temperature conditions suitable for maintaining desirable purity can appropriately be chosen. However, a borazine compound is usually preserved under a temperature condition of preferably not higher than 30° C., and more preferably not higher than 25° C. When a temperature condition on preserving a borazine compound exceeds 30° C., there is fear that impurities in a borazine compound are increased. Especially when an $R_2$ group in the above-described Chemical formula 1 is a hydrogen atom or a lower alkyl having a carbon number of 1 to 2, this problem is apt to be remarkably exhibited. In the above stated embodiment, a temperature condition on preservation of not higher than 30° C. most preferably extends the whole period from the beginning to the end of preservation, but it is not limited to only such an embodiment, and at least one point in the period from the beginning to the end of preservation, preferably in not shorter than 80% of the above described period, and more preferably in not shorter than 90% of the above described period, a temperature condition on preservation of not higher than 30° C. should be kept.

According to a container for preservation and a method for preservation using it of the present aspects, decomposition of a borazine compound on preservation can be suppressed, and decrease of purity of a borazine compound can be prevented to an extremely low extent. Namely, the present invention also provides a borazine compound wherein decrease of purity is suppressed. In this case, decrease of purity of a borazine compound provided by the present invention in case of preserving at 25° C. for 60 days is preferably not higher than 1% by mass, more preferably not higher than 0.1% by mass, and further preferably not higher than 0.01% by mass. Incidentally, "decrease of purity of a borazine compound is 1% by mass" means that purity of a borazine compound after preserving at 25° C. for 60 days is 98.8% by mass, for instance, in case where purity of a borazine compound at the beginning of preservation is 99.8% by mass. That means, "decrease of purity" does not mean a relative value before and after preservation, but means decrease of absolute purity of a borazine compound. Incidentally, as a value of purity of a borazine compound, a value measured by a method adopted in Examples as stated later is adopted.

Use of a borazine compound is not especially limited, but the compound can be used to form a low dielectric constant film such as an interlayer dielectric film for semiconductor, a barrier metal layer and an etch stopper layer. In such case, a borazine compound may be used or a compound derived from a borazine compound by modification may be used. A polymer obtained by polymerizing a borazine compound or a borazine compound derivative may be used as a raw material for an interlayer dielectric film for semiconductor, a barrier metal layer or an etch stopper layer.

A polymer can be formed with a compound having a borazine ring skeleton as a monomer. Polymerization method and polymerization mode are not especially limited. Polymerization method is selected depending on a functional group bonded to a borazine ring. For example, when an amino group is bonded, a polymer can be synthesized by condensation polymerization. When a vinyl group or a functional group containing a vinyl group is bonded to a borazine ring, a polymer can be formed by radical polymerization using a polymerization initiator. A polymer may be a homopolymer, or a copolymer containing two or more monomer units. Type of copolymer may be any of a random copolymer, a block copolymer, a graft copolymer, and the like. By using a monomer having three or more functional groups which can form a bond with other monomer, a polymer in which monomers are bonded together like a network can be obtained.

Next, a method for forming an interlayer dielectric film for semiconductor, a barrier metal layer or an etch stopper layer will be explained. In this connection, in the following description, "a borazine compound", "a borazine compound derivative" and "a polymer originated with them" are referred to as "a borazine-ring-containing compound".

To form an interlayer dielectric film for semiconductor, a barrier metal layer or an etch stopper layer using a borazine-ring-containing compound, a technique to form a coating film by preparing a composition in a solution state or a slurry state containing the borazine-ring-containing compound, and coating this composition. A solvent used in such a case for dissolving or dispersing the borazine-ring-containing compound is not especially limited as long as the solvent can dissolve or disperse the borazine-ring-containing compound or other component to be added, if necessary. As the solvent, for example, alcohols such as ethylene glycol and ethylene glycol monomerthyl ether; aromatic hydrocarbons such as toluene, benzene and xylene; hydrocarbons such as hexane, heptane and octane; tetrahydrofurane; diglyme; and tetraglyme, are used. These solvents may be used alone or in combination of two or more kinds. When film formation is performed using spin coating, diglyme is preferably used. By using diglyme or a derivative thereof as a solvent, a uniformity of a film to be produced is improved, and clouding of a film can be prevented. An amount of a solvent to be used for dissolving or dispersing the borazine-ring-containing compound is not especially limited, and may be determined corresponding to a production means for producing a low dielectric constant material. For example, when film formation is performed using spin coating, a kind and an amount of a solvent may be determined so that a viscosity becomes suitable for spin coating.

A composition containing the borazine-ring-containing compound is provided to a desired site, dried and solidified. For example, to form an interlayer dielectric film for semiconductor, the composition may be coated on a substrate by spin coating, and dried. When a film having a desired thickness cannot be obtained in one coating and drying, coating and drying may be repeated until a desired thickness is obtained. Film forming conditions such as number of revolutions of spin coater, drying temperature and drying time are not especially limited.

Coating on a substrate may be performed using a technique other than the spin coating. For example, spray coating and dip coating can be used.

After that, a coating film is dried. Drying temperature of a coating film is usually around 100 to 250° C. The "drying temperature" here means the highest temperature while drying treatment is carried out. For example, when a drying temperature is raised slowly, maintained at 100° C. for 30 min., and followed by cooling, a drying temperature is 100° C. Drying temperature can be measured using a thermo couple. Drying time for coating film is not especially limited, but may be determined, as appropriate, in consideration of characteristics such as dielectric constant and moisture resistance of a low dielectric constant material to be obtained.

EXAMPLES

Hereafter, embodiments of conducting the present invention are explained in detail by using Examples and Comparative Example, but technical scope of the present invention is not limited to the embodiments described below.

Example 1-1

Into a reaction vessel equipped with a cooler, while purging with nitrogen, methylamine hydrochloride (33.5 g) of an amine salt which was dehydration treated, and triglyme (98.6 g) which is a solvent were charged, and temperature of a reaction system was raised to 100° C.

On the other hand, sodium borohydride (21.0 g) which is an alkali boron hydride is prepared, this was added to triglyme (88.7 g) separately prepared, and thus a slurry was prepared.

The slurry of sodium borohydride prepared in the above described was added slowly over one hour to the reaction vessel which was raised to 100° C. as described above After the completion of the addition of slurry, reaction system was raised to 200° C. over 2 hours, and further was matured at 200° C. for 2 hours, to synthesize N,N',N"-trimethylborazine.

N,N',N"-trimethylborazine obtained was distilled at 150 to 220° C., to purify N,N',N"-trimethylborazine.

The N,N',N"-trimethylborazine purified was, under a nitrogen atmosphere at 23° C., cleanliness of 500 and a water content of 127 volume ppm., filtrated with a 0.1 µm filtration filter made of a polytetrafluoroethylene (PTFE) to further purify N,N',N"-trimethylborazine. In this connection, cleanliness of an atmosphere was measured with a particle counter (KC-03A1 manufactured by RION Co., Ltd.), and a water content was measured with an online dew point meter (manufactured by Nagano Electric Industial Co., Ltd.) (same in Examples hereinafter). Further, N,N',N"-trimethylborazine filtrated was filled into a container made of stainless steel which is possible to seal with a valve.

When a number of impurities having a particle diameter of not smaller than 0.5 µm contained in the purified N,N',N"-trimethylborazine filled into the container was measured with a particle counter (LIQUIL AZ-502-HF manufactured by Particle Measuring Systems Inc. (PMS Inc.)), a result thereof was 46 particles/mL. Further, when purity of the purified N,N',N"-trimethylborazine filled was measured, a result was 99.9% by mass. Incidentally, purity of a borazine compound was measured by gas chromatography. Measuring conditions were as follows.

Equipment: GC-14B manufactured by Shimadzu Corporation;
Column: Ultra Alloy (8H) manufactured by Hitachi Science Systems Ltd.;
Carrier gas: nitrogen;
Flow rate of carrier gas: 3.0 mL/min;
Sample injection temperature: 300° C.;
Detector temperature: 300° C.;
Sample injection amount: 0.2 µL; and
Column temperature: 50° C. (5 min)→raise temperature to 250° C. at a raising rate of 20° C./min→raise temperature to 300° C. at a raising rate of 10° C./min→300° C. (10 min).

Example 1-2

In the similar method to that of Example 1-1 described above, N,N',N"-trimethylborazine was synthesized, and was purified by distillation.

The N,N',N"-trimethylborazine purified was, under a nitrogen atmosphere at 23° C., cleanliness of 10, and a water content of 1 volume ppm., filtrated with a 0.1 µm filtration filter made of PTFE to further purify N,N',N"-trimethylborazine. Further, N,N',N"-trimethylborazine filtrated was filled into a container made of stainless steel which is possible to seal with a valve.

When a number of impurities having a particle diameter of not smaller than 0.5 µm contained in the purified N,N',N"-trimethylborazine filled into the container was measured with a particle counter (LIQUIL AZ-S02-HF manufactured by PMS Inc.), a result thereof was not more than 10 particles/mL. Further, when purity of the purified N,N',N"-trimethylborazine filled was measured, a result was 99.9% by mass.

Example 1-3

In the similar method to that of Example 1-1 described above, N,N',N"-trimethylborazine was synthesized, and was purified by distillation.

The N,N',N"-trimethylborazine purified was, under a nitrogen atmosphere at 23° C., cleanliness of 50000, and a water content of 127 volume ppm., filtrated with a 0.1 µm filtration filter made of PTFE to further purify N,N',N"-trimethylborazine. Further, N,N',N"-trimethylborazine filtrated was filled into a container made of stainless steel which is possible to seal with a valve.

When a number of impurities having a particle diameter of not smaller than 0.5 μm contained in the purified N,N',N"-trimethylborazine filled into the container was measured with a particle counter (LIQUIL AZ-S02-HF manufactured by PMS Inc.), a result thereof was not more than 73 particles/mL. Further, when purity of the purified N,N',N"-trimethylborazine filled was measured, a result was 99.8% by mass.

Comparative Example 1

In the similar method to that of Example 1-1 described above, N,N',N"-trimethylborazine was synthesized, and was purified by distillation.

The N,N',N"-trimethylborazine purified was, under a nitrogen atmosphere at 23° C., cleanliness of 50000, and a water content of 2570 volume ppm., filtrated with a 0.1 μm filtration filter made of PTFE to further purify N,N',N"-trimethylborazine. Further, N,N',N"-trimethylborazine filtrated was filled into a container made of stainless steel which is possible to seal with a valve.

When a number of impurities having a particle diameter of not smaller than 0.5 μm contained in the purified N,N',N"-trimethylborazine filled into the container was measured with a particle counter (LIQUIL AZ-S02-HF manufactured by PMS Inc.), a result thereof was not less than 3000/mL. Further, when purity of the purified N,N',N"-trimethylborazine filled was measured, a result was 97.5% by mass.

From the results shown in Example 1-1 to Example 1-3 and Comparative Example 1, it is shown that contamination of impurities into a borazine compound is effectively suppressed by filtrating and purifying a borazine compound under a specified atmospheric condition of water content or by filling it into a container under a specified atmospheric condition of water content.

Therefore, according to one aspect of the present invention, furthermore improvement of quality in uses wherein a borazine compound is used (for example, an interlayer dielectric film for semiconductor), is purposed for.

Example 2-1

Into a reaction vessel equipped with a cooler, while purging with nitrogen, methylamine hydrochloride (33.5 g) of an amine salt which was dehydration treated, and triglyme (98.6 g) which is a solvent were charged, and temperature of a reaction system was raised to 100° C.

On the other hand, sodium borohydride (21.0 g) which is an alkali boron hydride is prepared, this was added to triglyme (88.7 g) separately prepared, and thus a slurry was prepared.

The slurry of sodium borohydride prepared in the above described was added slowly over one hour to the reaction vessel which was raised to 100° C. as described above.

After the completion of the addition of slurry, a reaction system was raised to 200° C. over 2 hours, and further was matured at 200° C. for 2 hours, to synthesize N,N',N"-trimethylborazine.

N,N',N"-trimethylborazine obtained was distilled at 150 to 220° C., to purify N,N',N"-trimethylborazine. When purity of the purified N,N',N"-trimethylborazine obtained was measured, a result was 99.8% by mass. Incidentally, purity of a borazine compound was measured by gas chromatography. Measuring conditions are the same as those of Example 1-1.

As a container for preserving a borazine compound, a container of stainless steel the inner side of which was coated with PTFE (a thickness of the coating: 500 μm), was prepared. When withstanding pressure of a container for preservation prepared was measured, it was 0.2 MPa. In this case, measurement of withstanding pressure of a container for preservation was conducted as follows. Said container was provided with a leak valve, and a nitrogen gas was filled into said container at 23° C., and a filling pressure when a nitrogen gas begins to leak from said container through the leak valve, was measured by using a pressure gauge. Then, it was calculated by reducing a pressure of an atmosphere from the measured value.

The purified N,N',N"-trimethylborazine obtained as described above was filled into a container for preservation prepared and was sealed, and preserved at 25° C. for 60 days in a state of being pressurized by 0.1 MPa with a nitrogen gas. When purity of N,N',N"-trimethylborazine after the preservation was measured, it was 99.8% by mass, and thus decrease of purity of the borazine compound was not observed.

Example 2-2

Into a reaction vessel equipped with a cooler, B,B',B"-trichloro-N,N',N"-trimethylborazine (41.2 g) which is a halogenated borazine compound and diethyl ether (80 g) as a solvent were charged, and a diethyl ether solution of ethylmagnesium bromide (3 M, 200 mL) was added drop by drop at 20° C. over 3 hours. Subsequently, after being matured under a refluxing condition for 2 hours, a reaction solution was cooled to room temperature, and impurities were filtrated out by filtration.

Diethyl ether was distilled off from the filtrate obtained by filtration as described above, further filtration was conducted, and the filtrate was distilled at a reduced pressure to purify B,B',B"-triethyl-N,N',N"-trimethylborazine. When purity of B,B',B"-triethyl-N,N',N"-trimethylborazine obtained was measured in the same method as Example 1-1 described above, it was 99.5% by mass.

The purified B,B',B"-triethyl-N,N',N"-trimethylborazine obtained as described above was filled into the same container for preservation as that of Example 2-1 described above and was sealed, and preserved at 25° C. for 60 days in a state of being pressurized by 0.1 MPa with a nitrogen gas. When purity of B,B',B"-triethyl-N,N',N"-trimethylborazine after the preservation was measured, it was 99.5% by mass, and thus decrease of purity of the borazine compound was not observed.

Example 2-3

In the same method as Example 2-2 described above except that a temperature condition on preservation was set at 60° C., B,B',B"-triethyl-N,N',N"-trimethylborazine was synthesized, purified, and preserved. When purity of B,B',B"-triethyl-N,N',N"-trimethylborazine after the preservation was measured, it was 98.8% by mass, and thus decrease of purity of the borazine compound by 0.7% by mass was observed.

Comparative Example 2

In the same method as Example 2-1 described above, N,N',N"-trimethylborazine was synthesized, and purified by distillation.

As a container for preserving a borazine compound, a container of stainless steel the inner side of which was coated with PTFE (a thickness of the coating: 500 μm), was prepared. When withstanding pressure of a container for preservation prepared was measured, it was 0.05 MPa.

The purified N,N',N"-trimethylborazine obtained as described above was filled into a container for preservation prepared and was sealed, and preserved at 35° C. for 60 days. When purity of N,N',N"-trimethylborazine after the preservation was measured, it was 95.1% by mass, and thus decrease of purity of the borazine compound by 4.7% by mass was observed.

From the results shown in Examples 2-1 to 2-3, and Comparative Example 2 stated above, by preserving a borazine compound in a container for preservation having a specified withstanding pressure, it is shown that decomposition of a borazine compound can effectively be suppressed. Further, by conducting the preservation under a specified temperature condition, it is shown that decrease in purity of a borazine compound can effectively be suppressed.

Therefore, according to another aspect of the present invention, furthermore improvement of quality in uses wherein a borazine compound is used (for example, an interlayer dielectric film for semiconductor), is aimed for.

The present application is based on Japanese Patent Application No. 2005-241389 filed on Aug. 23, 2005 and Japanese Patent Application No. 2005-250074 filed on Aug. 30, 2005, and the disclosures are incorporated herein by reference in entirety.

What is claimed is:

1. A method for filling a borazine compound, the method comprising a filling step wherein a borazine compound is filled into a container having a withstanding pressure of not lower than 0.2 MPa under an atmospheric condition featuring a water content of not higher than 2000 volume ppm.

2. A method for filling according to claim 1, wherein the filling step is conducted under an atmospheric condition in which the number of foreign particles having a size of not smaller than 0.1 µm in 1 ft$^3$ is not higher than 1000.

3. A method for filling according to claim 1, wherein the borazine compound is a purified borazine compound produced by a production method comprising: (a) a preparation step wherein a borazine compound is prepared; and (b) a filtration step wherein the borazine compound prepared in step (a) is filtered under an atmospheric condition featuring a water content of not higher than 2000 volume ppm.

4. A method for filling according to claim 2, wherein the borazine compound is a purified borazine compound produced by a production method comprising: (a) a preparation step wherein a borazine compound is prepared; and (b) filtration step wherein the borazine compound prepared in step (a) is filtered under an atmospheric condition featuring a water content of not higher than 2000 volume ppm.

5. A method for filling according to claim 1, wherein a number of impurities having a particle diameter of not smaller than 0.5 µm, which are contained in the borazine compound, is not higher than 100 particles/mL.

6. A method for filling according to claim 2, wherein the borazine compound is a purified borazine compound produced by a production method comprising: (a) a preparation step wherein a borazine compound is prepared; and (b) a filtration step wherein the borazine compound prepared in step (a) is filtered under an atmospheric condition featuring a water content of not higher than 2000 volume ppm.

7. A method for filling according to claim 2, wherein a number of impurities having a particle diameter of not smaller than 0.5 µm, which are contained in the borazine compound, is not higher than 100 particles/mL.

8. A method for filling according to claim 3, wherein a number of impurities having a particle diameter of not smaller than 0.5 µm, which are contained in the borazine compound, is not higher than 100 particles/mL.

9. A method for filling according to claim 4, wherein a number of impurities having a particle diameter of not smaller than 0.5 µm, which are contained in the borazine compound, is not higher than 100 particles/mL.

10. A method for filling according to claim 6, wherein a number of impurities having a particle diameter of not smaller than 0.5 µm, which are contained in the borazine compound, is not higher than 100 particles/mL.

11. A method for filling according to claim 3, wherein the filtration step is conducted under an atmospheric condition in which the number of foreign particles having a size of not smaller than 0.1 µm in 1 ft$^3$ is not higher than 1000.

12. A method for filling according to claim 4, wherein the filtration step is conducted under an atmospheric condition in which the number of foreign particles having a size of not smaller than 0.1 µm in 1 ft$^3$ is not higher than 1000.

13. A method for filling according to claim 6, wherein the filtration step is conducted under an atmospheric condition in which the number of foreign particles having a size of not smaller than 0.1 µm in 1 ft$^3$ is not higher than 1000.

* * * * *